United States Patent [19]

Belliotti et al.

[11] Patent Number: 5,187,175
[45] Date of Patent: Feb. 16, 1993

[54] 2-CARBONYL SUBSTITUTED-5-HYDROXY-1,3-PYRIMIDINES AS ANTIINFLAMMATORY AGENTS

[75] Inventors: Thomas R. Belliotti, Ypsilanti; David T. Connor, Ann Arbor; Catherine R. Kostlan, Saline; Steven R. Miller, Ann Arbor, all of Mich.

[73] Assignee: Warner-Lambert Company, Morris Plains, N.J.

[21] Appl. No.: 847,511

[22] Filed: Mar. 6, 1992

[51] Int. Cl.$^5$ .................. C07D 239/36; A61K 31/505
[52] U.S. Cl. .................................... 514/269; 514/252; 514/241; 544/298; 544/295; 544/296; 544/238; 544/216
[58] Field of Search ............... 544/298, 295, 296, 238, 544/216; 514/269, 252, 241

[56] References Cited

U.S. PATENT DOCUMENTS 4,708,966 11/1987 Loomans et al. .................. 514/689
4,810,716 3/1989 Connor et al. ...................... 514/365
4,959,503 9/1990 Connor et al. ...................... 564/265
5,077,411 12/1991 Connor et al. ...................... 546/283

FOREIGN PATENT DOCUMENTS 0431659 6/1991 European Pat. Off. .

Primary Examiner—John M. Ford
Attorney, Agent, or Firm—Ronald A. Daignault

[57] ABSTRACT

The present invention is novel compounds which are 2-carbonyl substituted-5-hydroxy-1,3-pyrimidines and pharmaceutically acceptable acid addition or base salts thereof, pharmaceutical compositions and methods of use therefor. The invention compounds are now found to have activity as inhibitors of 5-lipoxygenase and/or cyclooxygenase providing treatment of conditions advantageously affected by such inhibition including inflammation, arthritis, pain, fever and the like. Thus, the present invention is also a pharmaceutical composition or method of manufacturing a pharmaceutical composition for the use of treating the noted conditions.

15 Claims, No Drawings

2-CARBONYL SUBSTITUTED-5-HYDROXY-1,3-PYRIMIDINES AS ANTIINFLAMMATORY AGENTS

BACKGROUND OF THE INVENTION

The present invention is novel compounds which are 2-substituted-5-hydroxy-1,3-pyrimidine derivatives and pharmaceutically acceptable acid addition or base salts thereof, pharmaceutical compositions and methods of use therefor, where a carbonyl group links the pyrimidine moiety to other residues. The compounds have activity as inhibitors of 5-lipoxygenase and/or cyclooxygenase providing treatment of conditions advantageously affected by such inhibition including, for example, rheumatoid arthritis, osteoarthritis, other inflammatory conditions, pain, fever, psoriasis, allergic diseases, asthma, inflammatory bowel disease, GI ulcers, cardiovascular conditions including ischemic heart disease and atherosclerosis, and ischemia-induced cell damage, particularly brain damage caused by stroke. They can also be used topically for treating acne, sunburn, psoriasis, and eczema. Also included are leukotriene mediated pulmonary, gastrointestinal, inflammatory, dermatological, and cardiovascular conditions. The disclosed compounds also have potential utility as antioxidants. However, overall the preferable use is to treat inflammatory conditions. Thus, the present inventory is also a pharmaceutical composition or method of manufacturing a pharmaceutical composition for the use of treating the noted conditions.

Numerous references describe 4-hydroxybenzenes optionally substituted by 3,5-dialkyl, e.g., ditertiarybutyl groups and linked to other groups by carbonyl as potential antiinflammatory agents because of their reported activity as inhibitors of 5-lipoxygenase and/or cyclooxygenase. These compounds are shown, for example, in U.S. Pat. Nos. 4,708,966, 4,810,716, 4,959,503, and 5,077,411. A particular compound, tebufelone, 1-[3,5-bis(1,1-dimethylethyl)-4-hydroxyphenyl]-5-hexyne-1-one, is described in European Publication Number 431,659. The replacement of a 4-hydroxybenzene by a heteroaromatic ring, particularly a 5-hydroxy-pyrimidine ring, is not described or suggested in any of the above references.

Various 5-hydroxypyrimidines are described in copending U.S. application Ser. Nos. 648,114, and 648,115 of Jan. 31, 1991 and U.S. Ser. No. 756,400 of Sep. 9, 1991. These compounds are also active as inhibitors of 5-lipoxygenase and/or cyclooxygenase. Such disclosed pyrimidines may also be substituted at the 4- and/or 6-positions with various groups including alkyls, e.g., tertiarybutyl in both the 4- and 6- positions. Yet, none of the above references show the present 2-substituent where either directly or interrupted by vinyl a carbonyl group links the 5-hydroxy-pyrimidines to other residues.

SUMMARY OF THE INVENTION

The present invention is a compound of the formula I

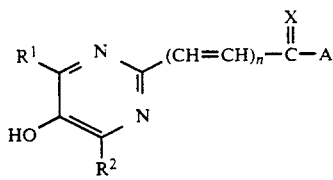

or pharmaceutically acceptable salt and hydrates thereof; wherein X is O or NOH; $R^1$ and $R^2$ are each independently hydrogen or lower alkyl; n is zero or one; and A is phenyl, substituted phenyl, $-CH_2OPh$, $-(CH_2)_mC\equiv CH$ in which m is an integer from two to four, or a 5- or 6-membered heteroaromatic ring 1) which ring contains 1, 2 or 3 heteroatoms selected from S, O, or N wherein the heteroaromatic ring may not have more than one of O or S, 2) which ring is attached at a carbon in the ring, and 3) which rings are optionally substituted by lower alkyl, preferably methyl. Of course the lower alkyl will be understood to be attached at one or more of the ring carbons.

The present invention is also a pharmaceutical composition for the treatment of conditions advantageously affected by the inhibition of 5-lipoxygenase alone or together with the inhibition of cyclooxygenase, preferably the inhibition of both 5-lipoxygenase and cyclooxygenase which comprises an amount effective for the treatment of the condition of a compound of the formula I and the pharmaceutically acceptable acid addition or base salt thereof together with a pharmaceutically acceptable carrier. The condition is meant to include, for example, rheumatoid arthritis, osteoarthritis, other inflammatory conditions, pain, fever, psoriasis, allergic diseases, asthma, inflammatory bowel disease, GI ulcers, cardiovascular conditions including ischemic heart disease and atherosclerosis, and ischemia-induced cell damage particularly brain damage caused by stroke. They can also be used topically for treating acne, sunburn, psoriasis, and eczema. Also included are leukotriene mediated pulmonary, gastrointestinal, inflammatory, dermatological, and cardiovascular conditions. The disclosed compounds also have potential utility as antioxidants. The preferred use is to treat inflammatory conditions.

The present invention is also a method for treatment of the condition as noted above in a mammal, including humans, suffering therefrom with a compound of the formula I or the pharmaceutically acceptable acid addition or base salt thereof, in unit dosage form. The invention also provides for use of any such compound of formula I or salt thereof in the manufacture of a medical therapeutic agent.

Pharmaceutical composition or use of the compound or salt of formula I is meant to include treatment understood to be prophylactic pertinent to the foregoing named condition.

DETAILED DESCRIPTION OF THE INVENTION

"Heteroaromatic ring" means pyridinyl, pyrimidinyl, thienyl, furyl, pyrrolyl, pyrazinyl, triazinyl, oxazolyl, isoxazolyl, pyrazolyl, pyridazinyl, imidazolyl, thiazolyl, isothiazolyl, thiadiazolyl, oxadiazolyl, triazolyl, and the like. These ring systems are meant to include rings having a lower alkyl substituent on one or more of the ring carbons, and also includes all possible regioisomers. Such regioisomers are limited by a required attachment to the remainder of the compound through a carbon of the ring.

"Substituted phenyl" means phenyl having one, two or three of lower alkyl, lower alkoxy, halogen, trifluoromethyl, $NR_{10}R_{11}$ wherein $R_{10}$ and $R_{11}$ are independently hydrogen or lower alkyl, $NO_2$, mercapto, hydroxy, or lower thioalkoxy.

In the compounds of formula I the term "lower alkyl", "lower alkoxy" or "lower thioalkoxy" includes an alkyl group of from one to six carbons such as methyl, ethyl, propyl, butyl, and the like and branched isomers thereof. Halogen is chloro, bromo or fluoro.

Ph stands for phenyl.

The compounds I of the invention may exist as tautomers which are readily determined from art recognized tautomerism.

Appropriate compounds of formula I are useful in the free base form, in the form of base salts where possible, and in the form of acid addition salts. The three forms are within the scope of the invention. In practice, use of the salt form amounts to use of the base form. Pharmaceutically acceptable salts within the scope of the invention may be those derived from mineral acids such as hydrochloric acid and sulfuric acid; and organic acids such as methanesulfonic acid, ethanesulfonic acid, benzenesulfonic acid, p-toluenesulfonic acid, and the like, giving the hydrochloride, sulfamate, methanesulfonate, ethanesulfonate, benzenesulfonate, p-toluenesulfonate and the like, respectively, or those derived from bases such as suitable organic and inorganic bases. Examples of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines such as methylamine, dimethylamine, and triethylamine; mono-, di-, or trihydroxyalkylamines such as mono-, di-, or triethanolamine; amino acids such as arginine and lysine; guanidine; choline N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.* 66(1):1-19 (1977).) Salts of inorganic bases include sodium, potassium, calcium or the like.

The acid addition salts of said basic compounds are prepared either by dissolving the free base or acid of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution. Salts can also be prepared by adding base to an aqueous alcohol solution of another salt.

The compounds of the invention may contain geometric isomers. Thus, the invention includes the individual isomers and mixtures thereof. The individual isomers may be prepared or isolated by methods known in the art.

The compounds of the present invention are also meant to include hydrated or solvated forms, if possible.

Preferred compounds of formula I are those wherein X is O or NOH; $R^1$ and $R^2$ are each tertiarybutyl; n is zero or one; and A is phenyl, phenyl substituted by lower alkyl, lower alkoxy, halogen, trifluoromethyl, $NR_{10}R_{11}$ wherein $R_{10}$ and $R_{11}$ are independently hydrogen or lower alkyl, $NO_2$, mercapto, hydroxy, or lower thioalkoxy, $-CH_2OPh$, $-(CH_2)_mC\equiv CH$ in which m is 3, or a heteroaromatic ring selected from pyridinyl, pyrimidinyl, thienyl, furyl, pyrrolyl, pyrazinyl, triazinyl, oxazolyl, isoxazolyl, pyrazolyl, pyridazinyl, imidazolyl, thiazolyl, isothiazolyl, thiadiazolyl, oxadiazolyl, or triazolyl.

More preferred are compounds of formula I wherein X is O or NOH; $R^1$ and $R^2$ are each tertiarybutyl; n is zero or one; and A is phenyl, $-CH_2OPh$, $-(CH_2)_3C\equiv CH$, thienyl, pyrazolyl, imidazolyl or thiazolyl.

Particularly valuable are:

1-[4,6-bis(1,1-dimethylethyl)-5-hydroxypyrimidin-2-yl]-4-phenoxy-1-butene-3-one;

1-[4,6-bis(1,1-dimethylethyl)-5-hydroxypyrimidin-2-yl]-4-phenoxy-1-butene-3-one oxime;

[4,6-[bis(1,1-dimethylethyl)]-5-hydroxy-2-pyrimidinyl]phenylmethanone;

Z-[4,6-bis(1,1-dimethylethyl)-5-hydroxy-2-pyrimidinyl]phenylmethanone, oxime;

[4,6-bis(1,1-dimethylethyl)-5-hydroxy-2-pyrimidinyl](2-thienyl)methanone;

1-[4,6-bis(1,1-dimethylethyl)-5-hydroxy-2-pyrimidinyl]-5 hexyn-1-one;

[4,6-bis(1,1-dimethylethyl)-5-hydroxy-2-pyrimidinyl](2 thiazolyl)methanone;

[4,6-bis(1,1-dimethylethyl)-5-hydroxy-2-pyrimidinyl](1H-imidazol-2-yl)methanone; and

[4,6-bis(1,1-dimethylethyl)-5-hydroxy-2-pyrimidinyl](1H-pyrazol-3-yl)methanone.

In determining when a lipoxygenase, cyclooxygenase, or dual lipoxygenase/cyclooxygenase inhibitor is indicated, of course inter alia, the particular condition in question and its severity, as well as the age, sex, weight, and the like of the subject to be treated, must be taken into consideration and this determination is within the skill of the attendant physician.

For medical use, the amount required of a compound of formula I or pharmacologically acceptable salt thereof to achieve a therapeutic effect will, of course, vary both with the particular compound, the route of administration, the mammal under treatment, and the particular disorder or disease concerned. A suitable dose of a compound of formula I or pharmacologically acceptable salt thereof for a mammal suffering from, or likely to suffer from any condition as described hereinbefore is 0.1 μg–500 mg of the compound per kilogram body weight. In the case of systemic administration, the dose may be in the range of 0.5 to 500 mg of the compound per kilogram body weight, the most preferred dosage being 0.5 to 50 mg/kg of mammal body weight administered two or three times daily. In the case of topical administration, e.g., to the skin or eye, a suitable dose may be in the range 0.1 ng–100 μg of the compound per kilogram, typically about 0.1 μg/kg.

In the case of oral dosing for the treatment or prophylaxis of arthritis or inflammation in general, due to any course, a suitable dose of a compound of formula I or physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example from 1 to 2 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of formula I or a pharmacologically acceptable acid addition or base salt thereof and a pharmacologically acceptable carrier therefor. Such formulations constitute a further feature of the present invention.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration. Such formulations are understood to include long acting formulations known in the art.

The formulations may conveniently be presented in unit dosage form and may be prepared by any of the methods well-known in the art of pharmacy All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in oil emulsion. The active ingredient may also be in the form of a bolus, electuary, or paste.

The usefulness of the compounds of the present invention as inhibitors of the 5 lipoxygenase enzyme, cyclooxygenase, or in treating related diseases or conditions may be demonstrated by their effectiveness in various standard test procedures. A description of each procedure follows.

ARBL/ARBC WHOLE CELL 5-LIPOXYGENASE AND CYCLOOXYGENASE ASSAYS

Materials

The rat basophilic leukemia cell line (RBL-1) was obtained from the American Type Culture Collection (Rockville, Md.).

Radioimmunoassay (RIA) kits of $LTB_4$ and $PGF_{2\alpha}$ were obtained from Amersham (Arlington Heights, Ill.) and Seragen (Boston, Mass.), respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate buffered saline pH 7.4 (PBS; NaCl, 7.1 g; $Na_2HPO_4$, 1.15 g; $KH_2PO_4$, 0.2 g; and KCl, 0.2 g/L). Cells are finally suspended in PBS containing 1.0 mM calcium at a density of $2 \times 10^6$ cells/mL. Cells are incubated with and without test agent (in DMSO) (1% DMSO is without effect on arachidonic acid metabolism) for ten minutes at room temperature. Calcium ionophore A23187 (5 $\mu$M) is added and cells are incubated for 7 minutes at 37° C. The reaction is stopped by chilling the tubes on ice for 10 minutes. Cells are separated by centrifugation and the supernatant is stored at $-20°$ C. Aliquots (100 $\mu$L) are analyzed for $LTB_4$ and $PGF_{2\alpha}$ using radioimmunoassay kits as provided by the supplier.

Carrageenan-Induced Rat Foot Paw Edema-2 (CFE-2) Assay: Protocol

Carrageenan solution (1% w/v) is prepared by dissolving 100 mg carrageenan (Marine Colloidal Div., Springfield, N.J.) in 10 mL of sterile saline (0.9%) solution (Travenol). The solution is vortexed for 30 to 45 minutes. Animals are dosed with compound 1 hour before carrageenan challenge. Foot paw edema is induced by injecting 0.10 mL of the 1% carrageenan subcutaneously into the plantar portion of the right hind paw of each rat under light anesthesia. Initial foot paw volume is measured immediately following carrageenan challenge using mercury plethysmography (Buxco Electronics). Edema is measured 5 hours after carrageenan. The difference between the 5-hour and the initial paw volume is expressed as delta edema. The delta edema for each test group of animals is used to calculate the percent inhibition of edema achieved by the compound at the test dose compared with the vehicle control group. The $ID_{40}$ (the dose at which swelling is inhibited by 40%) is calculated by probit analysis for the dose at which 40% inhibition occurs.

Mycobacterium-Induced Rat Footpad Edema Assay (MFE): Protocol

*Mycobacterium butyricum* (5 mg/mL) is suspended in paraffin oil by sonication for ten minutes in an ice bath. Footpad edema is induced on Day 0 by injecting 0.1 ml of the Mycobacterium mixture into the left hindpaw of lightly anesthetized rats. Swelling in the injected hindpaw is determined by mercury plethysmography 72 hours after injection. Groups of rats are treated with test compounds (suspended in 0.5% hydroxypropyl methylcellulose with 0.2% Tween-80) or vehicle one hour before Mycobacterium injection and on Days 1 and 2. Inhibition of swelling is determined by comparing the change in hindpaw volume in compound- and vehicle-treated rats. An $ID_{40}$ (the dose at which swelling is inhibited by 40%) is calculated by probit analysis.

Gastric Ulcerogenicity (UD): Protocol

Male outbred Wistar rats (100–250 g) are fasted for 24 hours. After fasting, test compounds are administered orally (in 2 mL/kg of 0.5% hydroxypropyl methylcellulose) and the rats are denied access to food and water for six more hours. The rats are then sacrificed with $CO_2$ so that the stomachs can be removed, opened along the greater curvature, and evaluated for the presence of gastric ulcers. Results are expressed as the percent of rats with gastric ulcers at a given dose or as the UD50 (the dose which causes ulcers in 50% of the rats).

In addition to the compounds of formula I, the pharmaceutical compositions can also contain other active ingredients, such as cyclooxygenase inhibitors, nonsteroidal antiinflammatory drugs (NSAIDs), peripheral analgesic agents such as zomepirac, diflunisal, and the like. The weight ratio of the compound of the formula I to the second active ingredient may be varied and will depend upon the effective dose of each ingredient. Generally, an effective dose of each will be used. Thus, for example, when a compound of the formula I is combined with an NSAID, the weight ratio of the compound of the formula I to the NSAID will generally range from about 1000:1 to about 1:1000, preferably about 200:1 to about 1:200. Combinations of a compound of the formula I and other active ingredients will generally also be within the aforementioned range, but in each case, an effective dose of each active ingredient should be used.

Combinations of a compound of the formula I and other active ingredients will generally be in the aforementioned ratios.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof.

The propionic acid derivatives which may be used comprise: ibuprofen, ibuprofen aluminum, indoprofen, ketoprofen, naproxen, benoxaprofen, flurbiprofen, fenoprofen, fenbufen, pirprofen, carprofen, oxaprozin, pranoprofen, miroprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Thus, "propionic acid derivatives" as defined herein are nonnarcotic analgesics/nonsteroidal antiinflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$NA$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are nonnarcotic analgesics/nonsteroidal antiinflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: mefanamic acid, meclofenamic acid, flufenamic acid, niflumic acid, and tolfenamic acid. Structurally related fenamic acid derivatives having similar analgesic and antiinflammatory properties are also intended to be encompassed by this group.

Thus, "fenamic acid derivatives" as defined herein are nonnarcotic analgesics/nonsteroidal antiinflammatory drugs which contain the basic structure:

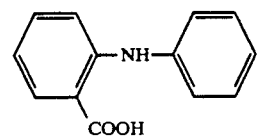

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/nonsteroidal antiinflammatory drugs which contain the basic structure:

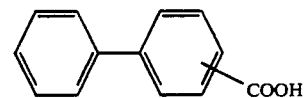

which can bear a variety of substituents and in which the free —COOH group can be in the form of a pharmaceutically acceptable salt group, e.g., —COO$^-$Na$^+$.

The oxicams which can be used in the present invention comprise: piroxicam, sudoxicam, isoxicam, and 4-hydroxyl-1,2-benzothiazine 1,1-dioxide 4-(N-phenyl)-carboxamide. Structurally related oxicams having similar analgesic and antiinflammatory properties are also intended to be encompassed by this group.

Thus, "oxicams" as defined herein are nonnarcotic analgesics/nonsteroidal antiinflammatory drugs which have the general formula:

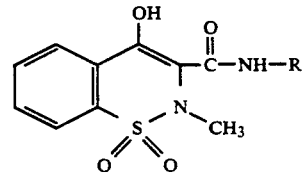

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, difisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin, clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

Finally, NSAIDs which may also be used include the salicylates, specifically aspirin, and the phenylbutazones, and pharmaceutically acceptable salts thereof.

Pharmaceutical compositions comprising the formula I compounds may also contain as the second active ingredient, antihistaminic agents such as benadryl, dramamine, histadyl, phenergan, and the like. Alternatively, they may include prostaglandin antagonists such as those disclosed in European Patent Application 11,067 or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the formula I may also be advantageously combined with an $H_1$ or $H_2$-receptor antagonist, such as for instance cimetidine, ranitidine, terfenadine, famotidine, temelastine, acrivastine, loratadine, cetrizine, tazifylline, azelastine, aminothiadiazoles disclosed in EP 81102976.8 and like compounds, such as those disclosed in U.S. Pat. Nos. 4,283,408; 4,362,736; 4,394,508, and European Patent Application No. 40,696. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

The compounds of the formula I and their salts are prepared generally by the following processes and constitute a further aspect of the present invention.

The compounds of the present invention of the formula I may be prepared as shown in Scheme I. In certain cases it may be necessary to protect the 5-hydroxy group of the pyrimidine using a suitable protecting group.

Examples of suitable oxygen protecting groups are benzyl, trialkylsilyl, ethoxyethyl, methoxyethoxymethyl, methoxymethyl, trialkylsilylethyl, and the like.

In the process described herein for the preparation of compounds of this invention the requirements for protective groups are generally well recognized by one skilled in the art of organic chemistry, and accordingly the use of appropriate protecting groups is necessarily implied by the processes of the charts herein, although such groups may not be expressly illustrated.

SCHEME I

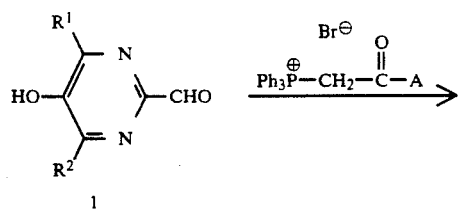

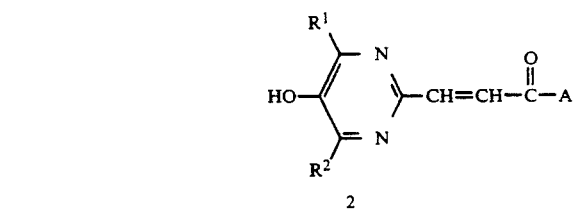

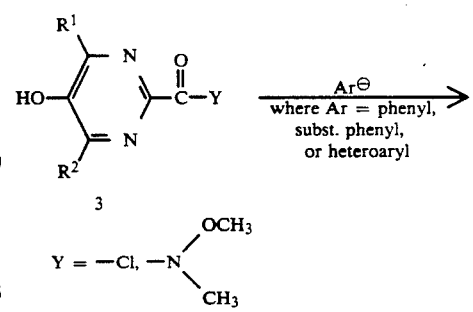

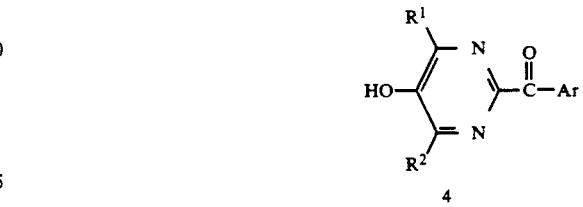

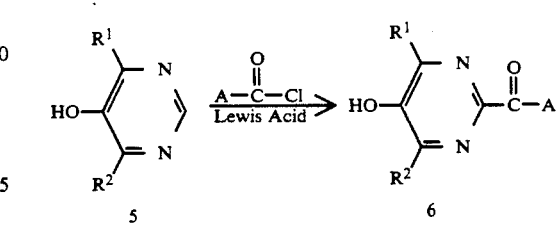

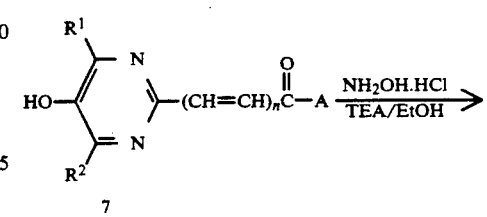

-continued
SCHEME 1

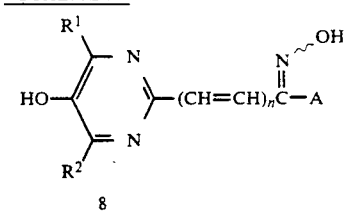

8

To prepare compounds of formula I where n is one, a pyrimidine-2-carboxaldehyde 1 is condensed with an appropriate triphenylphosphonium methylene bromide with the desired A group in the presence of a base such as potassium t-butoxide in a solvent such as tetrahydrofuran or toluene at a temperature of 0° C. to reflux for 1 to 24 hours to form the desired product 2.

To prepare compounds of formula I where n is zero and A is phenyl, substituted phenyl or a heteroaromatic ring, Ar, a pyrimidine-2-acid chloride 3 or a 2-(N-methoxy-N-methyl-acyl)pyrimidine 3 is reacted with the desired Ar group under conditions that generate Ar⁻ to form a compound 4.

Compounds of formula I where n is zero and A is as generally defined above may also be prepared by an alternative Friedel Crafts reaction on the 5-hydroxypyrimidine 5 with the desired acid chloride,

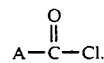

in the presence of a Lewis Acid, e.g., aluminum chloride, boron trifluoride, zinc chloride and like reagents to form the desired compound 6.

The oximes of the compounds of formula I, i.e., X is NOH, may be prepared by reacting compound 7, which includes any combination of compounds 2, 4, or 6 in Scheme I, with hydroxylamine-hydrochloride in the presence of a base, preferably a tertiary amine, e.g., triethylamine, in an alcoholic solvent, e.g., ethanol, at room temperature or up to the boiling point of the solvent.

Compound 9 in Scheme II is treated with sodium cyanide to replace the 2-thiomethyl group. Reduction of the cyano group with diisobutylaluminum hydride, DIBAL, affords the desired aldehyde 1. Treatment of the 2-cyano-pyrimidine with base, e.g., sodium hydroxide, followed by neutralization provides the 2-carboxylic acid which can be decarboxylated at elevated temperatures to form pyrimidine 5 or treated with thionyl chloride or other known halogenating agents to form the acid chloride 3, not shown in Scheme II. The pyrimidine-2-carboxylic acid may also be converted to pyrimidine 3 where the acylating agent is the N-methoxy-N-methylformyl group by treating the carboxylic acid in the presence of carbodiimide with N-methyl-N-methoxyamine.

SCHEME II

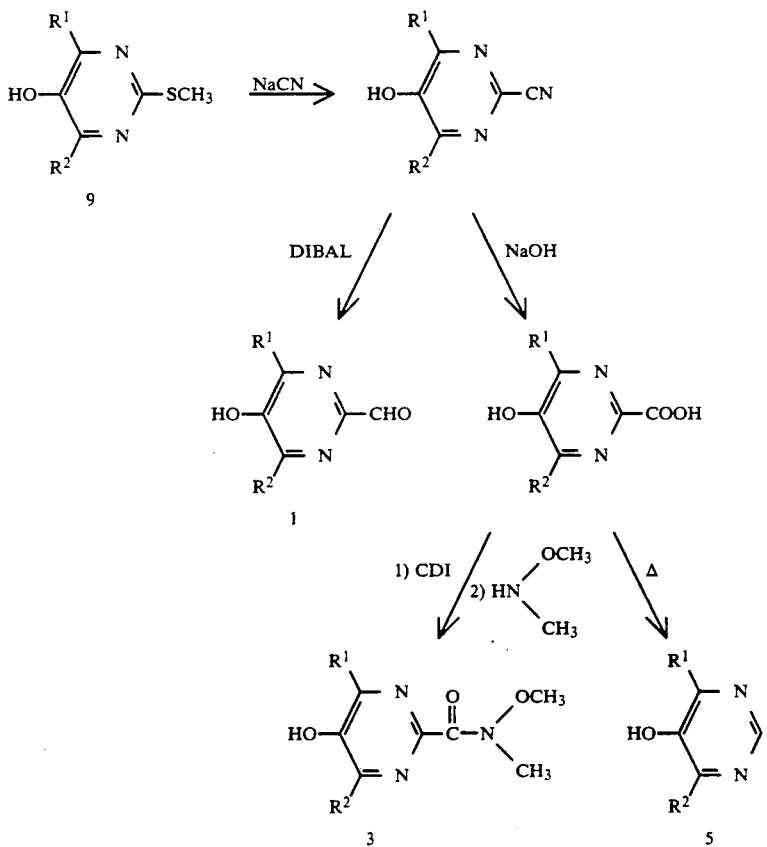

The starting materials used to prepare the compounds of formula I may be prepared as follows: pyrimidines 1, 3, and 5 of Scheme 1 where $R^1$ or $R^2$ are H or lower alkyl other than tertiarybutyl may be prepared as shown in Scheme II from pyrimidines 9 which may be prepared as described by Hurst (*Heterocycles* 22(1), (1984)) for $R^1 = R^2 =$ methyl.

Starting pyrimidines 1, 3, and 5 of Scheme I where $R^1$ and $R^2$ are tertiarybutyl may be prepared as shown in Scheme III.

Compound of the formula 10 in Scheme III is prepared from the known haloketone (C. W. Shoppee and D. Stevenson, *J. Chem. Soc. Perking I*, p. 3015, 1972) by reaction with a salt of acetic acid such as sodium or potassium acetate in a solvent such as DMSO at a reaction temperature of 18° C. to 60° C., or in a solvent such as acetic acid at reflux. Acetoxydiketone 10 is converted to oxazole 11 by treatment with an ammonium salt such as ammonium chloride or preferably ammonium acetate in a solvent such as acetic acid at reflux for 1 to 16 hours or in a solvent such as formamide at 100°

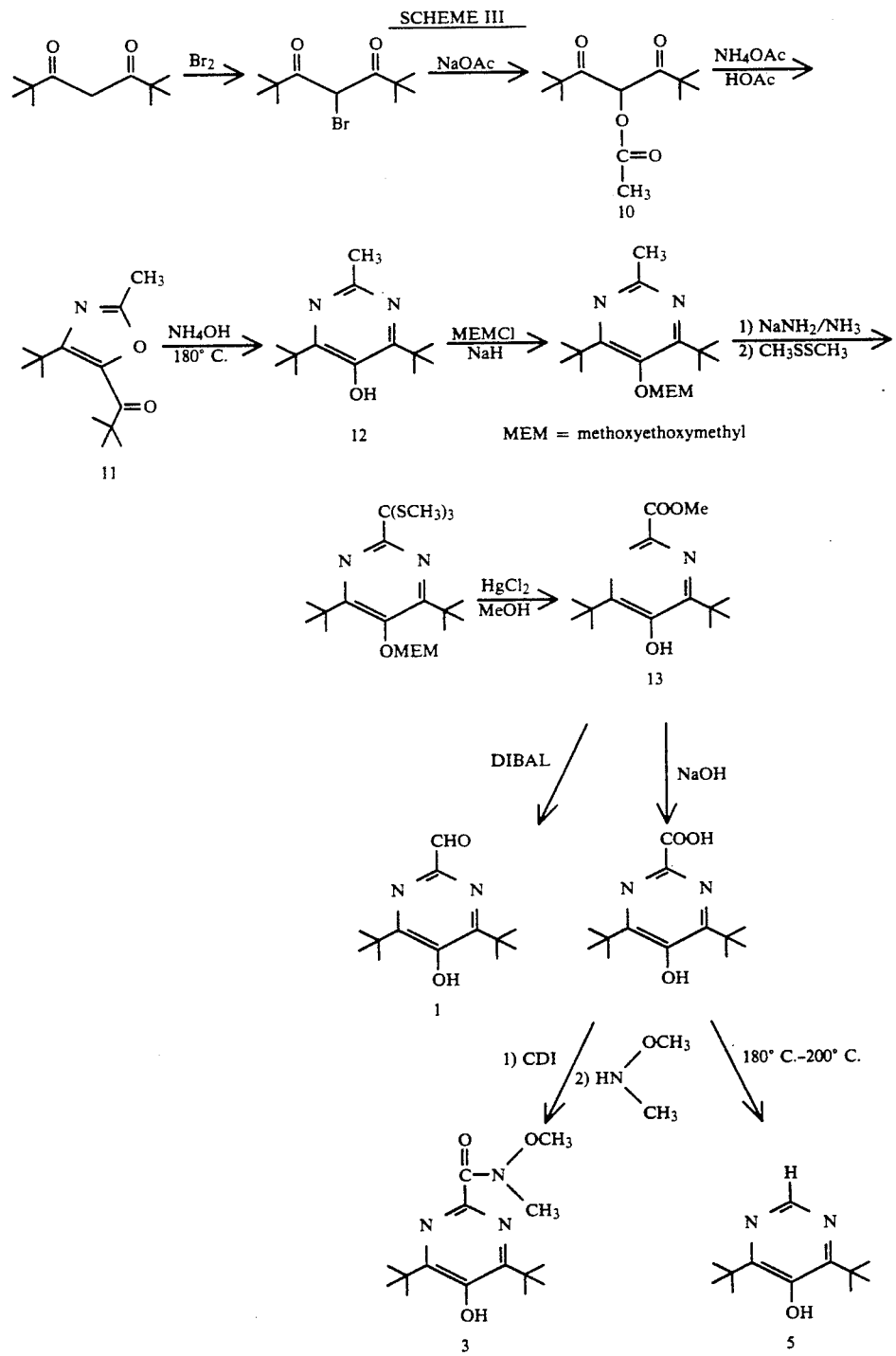

to 200° C. for 1 to 6 hours. The oxazole 11 is converted to pyrimidine 12 by treatment with ammonia or an ammonium salt at elevated temperature. Preferably 11 is reacted with concentrated ammonium hydroxide at 150° to 190° C. in a pressure reaction vessel for 6 to 72 hours.

Pyrimidine 12 is then converted to the 2-carboxymethyl ester of the desired pyrimidine 13 in three steps which requires protection of the 5-hydroxy group, converting the 2-methyl group first to the methyl thioortho ester and hydrolysis with mercuric chloride in methanol to provide the desired ester. The ester 13 may be directly converted to the desired aldehyde starting material 1 of Scheme I by reducing the carboxymethyl group with diisobutylaluminum hydride, DIBAL. Alternatively, hydrolysis of ester 13 with base, e.g., sodium hydroxide, gives the corresponding carboxylic acid which may, in turn, be converted to pyrimidines 3 and 5 of Scheme I similarly as shown in Scheme II.

The products of the reactions described herein are isolated by conventional means such as extraction, distillation, chromatography, and the like.

The invention is further elaborated by the representative examples as follows.

EXAMPLE 1

1-[4,6-Bis(1,1-dimethylethyl)-5-hydroxypyrimidin-2-yl]-4-phenoxy-1-butene-3-one

A solution of 4,6-bis(1,1-dimethylethyl)-5-hydroxypyrimidine-2-carboxaldehyde (1.5 g, 6.3 mmol) (PD-4287-01-JT) and 1-triphenyl phosphoranylidene-3-phenoxy-2-propanone (2.6 g, 6.3 mmol) in 50 mL of toluene is warmed to reflux for 18 hours. The toluene is evaporated. The remaining solid is dissolved in a minimum amount of ethyl acetate, and adsorbed onto a pad of silica gel. Elution with 20% ether/hexane followed by evaporation of the eluant gives an off-white solid. Recrystallization from hexane gives 1.4 g (60%) of 1-[4,6-bis(1,1-dimethylethyl)-5-hydroxy pyrimidin-2-yl]-4-phenoxy-1-butene-3 one, mp 98°–100° C.

Analysis for $C_{22}H_{28}N_2O_3$: Calcd: C, 71.71; H, 7.66; N, 7.60; Found: C, 71.72; H, 7.54; N, 7.49.

EXAMPLE 2

1-[4,6-Bis(1,1-dimethylethyl)-5-hydroxypyrimidin-2-yl]-4-phenoxy-1-butene-3-one oxime 1-[4,6-Bis(1,1-dimethylethyl)-5-hydroxypyrimidin-2-yl]-4-phenoxy-1-butene-3-one (0.7 g, 1.9 mmol) is added to an ethanolic (50 mL) solution of hydroxylamine hydrochloride (1.3 g, 19 mmol) and sodium acetate (1.7 g, 20.9 mmol). The reaction mixture is stirred at room temperature under argon for 18 hours. The ethanol is evaporated under reduced pressure, and the remaining solid is partitioned between 20 mL of water and 20 mL of ethyl acetate. The layers are separated and the aqueous phase is washed with ethyl acetate (3×20 mL). The combined organic layers are washed with water (3×20 mL) and 20 mL of brine. Drying over $MgSO_4$ followed by evaporation of solvent gives a yellow oil. Flash chromatography (silica, methylene chloride) followed by recrystallization from hexane gives 0.21 g (29%) of 1-[4,6-bis(1,1-dimethylethyl)-5-hydroxypyrimidin-2-yl]-4-phenoxy-1-butene-3-one oxime, mp 130°–135° C.

Analysis for $C_{22}H_{29}N_3O_3$: Calcd: C, 68.90; H, 7.62; N, 10.96; Found: C, 68.96; H, 7.69; N, 10.75.

EXAMPLE 3

4,6-Bis(1,1-dimethylethyl)-5-hydroxy-N-methoxy-N-methyl-2-pyrimidinecarboxamide

To a slurry of 4,6-bis(1,1-dimethylethyl)-5-hydroxy-2-pyrimidine carboxylic acid (6.20 g, 24.6 mmol) and N,N-dimethylformamide (0.10 mL, 1.3 mmol) in dichloromethane (200 mL) at ~0° C. under nitrogen atmosphere is added oxalyl chloride (3.30 mL, 37.8 mmol) dropwise. The resulting mixture is stirred 1 hour at 0° C., warmed to room temperature, and stirred an additional 2 hours. The solvent is removed under vacuum and tetrahydrofuran (200 mL) added to the residue. This mixture is cooled to ~0° C. and a solution of N,O-dimethyl-hydroxylamine hydrochloride (2.64 g, 27.1 mmol) and 1-methylpiperidine (3.30 mL, 27.2 mmol) in dichloromethane (100 mL) is added dropwise. After warming to room temperature, the mixture is stirred 16 hours, diluted with dichloromethane (200 mL), and washed with aqueous 0.1N HCl, saturated sodium bicarbonate, and brine solutions. The organic layer is concentrated and the residue recrystallized from ethyl acetate and hexane to give 4.26 g (58%) of the title compound, mp 137°–138° C.

EXAMPLE 4

[4,6-Bis(1,1-dimethylethyl)-5-hydroxy-2-pyrimidinyl]phenylmethanone

To a solution of 4,6-bis(1,1-dimethylethyl)-5-hydroxy-N-methoxy-N-methyl-2-pyrimidinecarboxamine (0.50 g, 1.7 mmol) in tetrahydrofuran (10 mL) at ~0° C. under nitrogen atmosphere is added a 0.84M solution of phenylmagnesium bromide in ethyl ether (4.0 mL, 3.4 mmol) dropwise. The resulting mixture is stirred for 1 hour at ~0° C., warmed to room temperature and stirred 20 hours. This mixture is then quenched with saturated aqueous ammonium chloride solution and extracted with ethyl acetate. The combined organic extracts are washed with water and brine solution and then concentrated under vacuum. The organic residue is purified by flash chromatography ($SiO_2$, dichloromethane) followed by recrystallization from petroleum ether and ethyl ether to give 0.36 g (68%) of the title compound, mp 129°–131° C.

EXAMPLE 5

Z-[4,6-Bis(1,1-dimethylethyl)-5-hydroxypyrimidin-2-yl]phenylmethanone, oxime

To a solution of [4,6-bis(1,1-dimethylethyl)-5-hydroxy-2-pyrimidinyl]phenylmethanone (0.90 g, 2.9 mmol) in pyridine (15 mL) is added hydroxylamine hydrochloride (0.30 g, 4.3 mmol). This mixture is warmed to reflux, refluxed 3 hours, and cooled to room temperature. The solvent is removed under vacuum and the organic residue dissolved in ethyl ether (20 mL) and filtered. The filtrate is washed with water and brine solution, and then concentrated. The residue is recrystallized from methanol and water to give 0.64 g (68%) of the title compound, mp 171°–176° C. decomposes.

EXAMPLE 6

[4,6-Bis(1,1-dimethylethyl)-5-hydroxy-2-pyrimidinyl](2-thienyl)methanone

To a mixture of magnesium turnings (1.22 g, 50.7 mmol) in dry ethyl ether (16 mL) under nitrogen atmosphere is added a single crystal of iodine followed by freshly distilled 2-bromothiophene (2.50 mL, 30.0 mmol) dropwise over 1 hour. This mixture is refluxed 1 hour then cooled to room temperature. The molarity of the solution (1.06M) is determined by titration of a small sample with isopropanol. A portion of this 1.06M solution of thiophene magnesium bromide in ether (3.5 mL, 3.71 mmol) is added dropwise under nitrogen atmosphere to a solution of 4,6-bis(1,1-dimethylethyl)-5-hydroxy-N-methoxy-N-methyl-2-pyrimidinecarboxamide (0.50 g, 1.7 mmol) in tetrahydrofuran (15 mL) dropwise. The resulting mixture is stirred 16 hours, diluted with ethyl ether (15 mL), quenched with aqueous saturated ammonium chloride solution, and washed with water and brine solution. Concentration of the organic phase followed by purification by flash chromatography ($SiO_2$, dichloromethane) and recrystallization from methanol and water gave 0.40 g (74%) of title compound, mp 157.5°–159° C.

EXAMPLE 7

1-[4,6-Bis(1,1-dimethylethyl)-5-hydroxy-2-pyrimidinyl]-5-hexyn-1-one

A mixture of 1-[4,6-bis(1,1-dimethylethyl)-5-hydroxypyrimidin-2-yl]-6-trimethylsilyl-5-hexyn-1-one (0.87 g, 2.3 mmol), Example 8, and potassium fluoride dihydrate (0.91 g, 9.7 mmol) in N,N-dimethylformamide (12 mL) is warmed to 50° C. After stirring for 47 hours at 50° C., the solvent is removed under vacuum and the organic residue is diluted with water. This mixture is extracted with ethyl acetate and the combined extracts are washed with saturated aqueous ammonium chloride solution and brine. The organic is concentrated under vacuum and the organic residue purified by flash chromatorgraphy ($SiO_2$, 20% ethyl acetate (hexane) followed by recrystallization from methanol and water to give 0.48 g (68%) of the title compound), mp 64°–66° C.

EXAMPLE 8

1-[4,6-Bis(1,1-dimethylethyl)-5-hydroxy-2-pyrimidinyl]-6-trimethylsilyl-5-hexyn-1-one To a solution of 4,6-bis(1,1-dimethylethyl)-5-hydroxy-N-methoxy-N-methyl-2-pyrimidinecarboxamide (1,00 g, 3.38 mmols) in tetrahydrofuran (50 mL) under nitrogen atmosphere is added a freshly prepared 0.105M solution of 5-trimethylsilylpent-4-ynyl magnesium bromide (81 mL, 8.5 mmols) [from 5-bromo-1-trimethylsilyl-1pentyne (3.86 g, 17.5 mmol) and magnesium (1.50 g, 61.7 mg-atom) in tetrahydrofuran (140 mL)] dropwise. After stirring 16 hours, the resulting mixture is quenched with saturated aqueous ammonium chloride solution and extracted with ethyl ether. The combined extracts are washed with brine and the organic phase is dried over magnesium sulfate. Concentration under vacuum is followed by purification of the organic residue by flash chromatography ($SiO_2$, 20% ethyl acetate/hexane) to give 0.97 g (77%) of the title compound which is used without further purification to make the compound of Example 7.

EXAMPLE 9

[4,6-Bis(1,1-dimethylethyl)-5-hydroxy-2-pyrimidinyl](2-thiazolyl)methanone

To a solution of diisopropylamine (0.39 mL, 4.2 mmol) in tetrahydrofuran (8 mL) at −78° C. under nitrogen atmosphere is added a 2.1M solution of n-butyllithium (2.0 mL, 4.2 mmol) in cyclohexane. This mixture is stirred at −78° C. for 1 hour and thiazole (0.3 mL, 4.2 mmol) added. After stirring 1 hour at −78° C., the reaction mixture is warmed to ~0° C. and stirred 0.5 hours. The mixture is cooled to −78° and 4,6-bis(1,1-dimethylethyl)-5-hydroxy-N-methoxy-N-methyl-2-pyrimidinecarboxamide (0.50 g, 1.7 mmol) in a mixture of tetrahydrofuran (5 mL) and N,N,N'N'-tetramethylethylenediamine (2 mL). After stirring 1 hour at 78° C., the resulting mixture is warmed to room temperature and stirred 16 hours. The mixture is then quenched with aqueous ammonium chloride solution and extracted with ethyl acetate. The combined extracts are washed with water and brine. The organic phase is dried over magnesium sulfate and concentrated under vacuum. The organic residue is purified by flash chromatography ($SiO_2$, 10% methanol/dichloromethane) followed by recrystallization from ethyl acetate and hexane to give 0.30 g (53%) of the title compound, mp 181°–184° C.

EXAMPLE 10

[4,6-Bis(1,1-dimethylethyl)-5-hydroxy-2-pyrimidinyl](1H-imidazol-2-yl)methanone

To a solution of 1-[(dimethylamino)methyl]imidazole (0.70 g, 5.6 mmol) (See Katritzky, A. R.; Rewcastle, G. W.; Fan, W-Q; *J. Org. Chem.* 1988, 53, 5688) in tetrahydrofuran (10 mL) at −78° C. under nitrogen atmosphere is added a 1.58M solution of n-butyllithium (3.60 mL, 5.69 mmol) in hexanes dropwise. The resulting mixture is stirred 1 hour at −78° C., warmed to ~0° C., and stirred 0.5 hours. After cooling to −78° C., 4,6-bis(1,1-dimethylethyl)-5-hydroxy-N-methoxy-N-methyl-2-pyrimidinecarboxamide (0.50 g, 1.7 mmol) in tetrahydrofuran (5 mL) is added. This mixture is warmed to room temperature, stirred for 16 hours, and quenched by addition of aqueous 2N hydrochloric acid solution. After extraction with ethyl acetate, the combined extracts are washed with water and brine solution. Concentration of the organic phase under vacuum followed by recrystallization of the organic residue from methanol and water gives 0.43 g (84%) of the title compound, mp 217°–220° C.

EXAMPLE 11

[4,6-Bis(1,1-dimethylethyl)-5-hydroxy-2-pyrimidinyl](1H-pyrazol-3-yl)methanone

To a solution of 1-(1-pyrrolidinomethyl)pyrazole (0.64 g, 4.2 mmol) (See Katritzky, A. R.; Rewcastle, G. W.; Fan, W-Q; *J. Org. Chem* 1988, 53, 5688) in tetrahydrofuran (10 mL) at −78° C. under nitrogen atmosphere is added a 2.1M solution of n-butyllithium (2.0 mL, 4.20 mmol) in cyclohexane. The resulting mixture is stirred 1 hour at −78° C. and warmed to ~0° C. After stirring 0.5 hours at 0° C., this mixture is cannula transferred to a solution of 4,6-bis(1,1-dimethylethyl)-5-hydroxy-N-methoxy-N-methyl-2-pyrimidinecarboxamide in tetrahydrofuran (10 mL) at ~0° C. This reaction mixture is warmed to room temperature and stirred 16 hours. After quenching with aqueous saturated ammonium chloride solution, the mixture is extracted with ethyl acetate and the combined extracts washed with brine. The organic phase is dried over magnesium sulfate and concentrated under vacuum. The organic residue is purified by flash chromatography ($SiO_2$, 10% methanol/hexane) followed by recrystallization from isopropanol and water to give 0.22 g (43%) of title compound as a mixture of tautomers, mp 156°–161° C.

We claim:
1. A compound of the formula

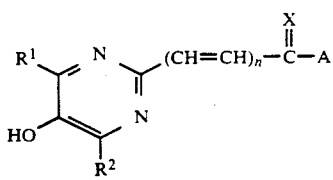

or a pharmaceutically acceptable salt, or hydrate thereof; wherein X is O or NOH; $R^1$ and $R^2$ are each independently hydrogen or lower alkyl; n is an integer of zero or one; and A is phenyl, phenyl substituted by lower alkyl, lower alkoxy, halogen, trifluoromethyl, $NR_{10}R_{11}$ wherein $R_{10}$ and $R_{11}$ are independently hydrogen or lower alkyl, $NO_2$, mercapto, hydroxy, or lower thioalkoxy, —$CH_2OPh$, —$(CH_2)_mC\equiv CH$ in which m is an integer from two to four, or a 5 or 6 membered heteroaromatic ring 1) selected from pyridinyl, pyrimidinyl, thienyl, furyl, pyrrolyl, pyrazinyl, triazinyl, oxazolyl, isoxazolyl, pyrazolyl, pyridazinyl, imidazolyl, isothiazolyl, thiazolyl, thiadiazolyl, oxadiazolyl, and triazolyl, 2) which ring is attached at a carbon in the ring, and 3) which ring is optionally substituted by lower alkyl.

2. A compound of claim 1 wherein $R^1$ and $R^2$ are tertiarybutyl.

3. A compound of claim 2 wherein a is phenyl, phenyl substituted, by lower alkyl, lower alkoxy, halogen, trifluoromethyl, $NR_{10}R_{11}$ wherein $R_{10}$ and $R_{11}$ are independently hydrogen or lower alkyl, $NO_2$, mercapto, hydroxy, or lower thioalkoxy, $CH_2OPh$, —$(CH_2)_mC\equiv CH$ in which m is three, or a 5- or 6-membered heteroaromatic ring selected from pyridinyl, pyrimidinyl, thienyl, furyl, pyrrolyl, pyrazinyl, triazinyl, oxazolyl, isoxazolyl, pyrazolyl, pyridazinyl, imidazolyl, isothiazolyl, thiazolyl, thiadiazolyl, oxadiazolyl, and triazolyl.

4. A compound of claim 3 wherein A is phenyl, —$CH_2OPh$, —$(CH_2)_3C\equiv CH$, thienyl, pyrazolyl, imidazolyl or thiazolyl.

5. A compound of claim 4 and being 1-[4,6-bis(1,1-dimethylethyl)-5-hydroxypyrimidin-2-yl]-4-phenoxy-1-butene-3-one.

6. A compound of claim 4 and being 1-[4,6-bis(1,1-dimethylethyl)-5-hydroxypyrimidin-2-yl]-4-phenoxy-1-butene-3-one oxime.

7. A compound of claim 4 and being [4,6-bis(1,1-dimethylethyl)-5-hydroxy-2-pyrimidinyl]-phenylmethanone.

8. A compound of claim 4 and being Z-[4,6-bis(1,1-dimethylethyl)-5-hydroxy-2-pyrimidinyl]-phenylmethanone oxime.

9. A compound of claim 4 and being [4,6-bis(1,1-dimethylethyl)-5-hydroxy-2-pyrimidinyl](2-thienyl)methanone.

10. A compound of claim 4 and being 1-[4,6-bis(1,1-dimethylethyl)-5-hydroxy-2-pyrimidinyl]-5-hexyn-1-one.

11. A compound of claim 4 and being [4,6-bis(1,1-dimethylethyl)-5-hydroxy-2-pyrimidinyl](2-thiazolyl)methanone.

12. A compound of claim 4 and being [4,6-bis(1,1-dimethylethyl)-5-hydroxy-2-pyrimidinyl](1H-imidazol-2-yl)methanone.

13. A compound of claim 4 and being [4,6-bis(1,1-dimethylethyl)-5-hydroxy-2-pyrimidinyl](1H-pyrazol-3-yl)methanone.

14. A pharmaceutical composition for the treatment of a condition advantageously affected by the inhibition of 5-lipoxygenase, cyclooxygenase or both 5-lipoxygenase and cyclooxygenase which comprises an amount effective for the treatment of the condition of the compound of claim 1 and a pharmaceutically acceptable carrier.

15. A method of treating inflammation in a human in need of such treatment which comprises administering a composition of claim 14 in unit dosage form.

* * * * *